United States Patent [19]

Usrey

[11] Plant 5,212

[45] Mar. 27, 1984

[54] *RAPHIOLEPIS INDICA* CV. MONRUCE

[75] Inventor: William B. Usrey, Glendora, Calif.

[73] Assignee: Monrovia Nursery Company, Azusa, Calif.

[21] Appl. No.: 411,825

[22] Filed: Aug. 26, 1982

[51] Int. Cl.[3] ..... A01H 5/00

[52] U.S. Cl. ..... Plt./54

[58] Field of Search ..... Plt./54

*Primary Examiner*—Robert E. Bagwill

[57] ABSTRACT

A new and distinct selection of *Raphiolepis indica* (L.) Lindl. shrub (known popularly as Indian Hawthorn) which shall be referred to hereinafter as *Raphiolepis indica* cultivar Monruce. *Raphiolepis indica* cultivar Monruce differs distinctively from its parent, *Raphiolepis indica* cultivar Enchantress by my new selection having a more dense growth habit, a compact inflorescence, and double flowers with large spreading light pink petals.

2 Drawing Figures

DISCOVERY

This invention relates to a new and distinct selection of *Raphiolepis indica,* a member of the rose family, Rosaceae. *Raphiolepis indica* cv. Monruce was discovered as a chance seedling among *Raphiolepis indica* 'Enchantress' at Monrovia Nursery Company, 18331 E. Foothill Boulevard, Azusa, Calif. in April of 1976.

The plant to date is known to exist only within the boundaries of Monrovia Nursery and has not been offered for sale or described in any publication.

REPRODUCTION

My new selection has been strictly asexually reproduced by cuttings at Monrovia Nursery Company. The distinct phenotypic characteristics of this selection that set this plant apart from the parent plant would be lost genetically through sexual reproduction. Therefore, propagation is restricted to asexual reproduction and sexual reproduction is prohibited.

CHARACTERISTICS

The accompanying illustrations show a typical specimen of the plant according to this invention and are depicted in color as nearly true as possible.

*Raphiolepis indica* cv. Monruce differs from its parent *Raphiolepis indica* cv. Enchantress in its distinct open double flowers with large pink petals and a more dense inflorescence. These attributes of our new selection are shown in the lower photograph.

The upper photograph displays the dense compact overall growth habit of my new selection.

My new selection, *Raphiolepis indica* cv. Monruce was deliberately selected for the attributes mentioned above and shown in the accompanying photos.

DESCRIPTION

Below is a detailed description of the new *Raphiolepis indica* cv. Monruce, the color terminology is from the British Horticultural Colour Charts.

Overall size and habit: Evergreen, dense, at maturity (3–4 yrs.) plant approximately 3 feet in height and width.

Foliage:

*Size.*—1 to 1¾" wide and 2 to 2½" in width.

*Shape.*—Variable, narrow to wide elliptic to wide spatulate, tip acuminate to mucronate, base attenuate.

*Color.*—Upper surface — Spinach Green 0960. Lower surface — Fern Green 0862/1.

*Margins.*—Upper two thirds — serrate. Lower one third — entire.

*Texture.*—Coriaceous.

*Arrangement.*—Alternate.

*Pubescence.*—Young growth wooly pubescent mature growth completely glabrous.

*Petioles.*—½ to ¾ inch in length. Fern Green 0862/1. Slightly pubescent.

Inflorescence:

*Size.*—2 to 3½" wide. 2½ to 4" long.

*Shape.*—Dense, broad pyramidal panicle.

*Flower color.*—Inner center — white. Petal tips and outer portion — Rhodamine Pink 527/3. Inner petals — blushed with darker Rhodamine Pink 527/2. Fading to white with age.

*Petal size.*—¼ to ⅜" in length. 3/16 to ¼" in width.

*Petal shape.*—Spatulate to obovate.

*Petal margin.*—Slightly laciniate at top; tip emarginate sometimes mucronate.

*Petal number.*—Double flower. 7 to 10 petals per flower are generally constant.

*Peduncle.*—⅜" in length, wooly pubescent.

I claim:

1. A new and distinct selection of Raphiolepis as substantially shown and described herein, that is characterized by a dense growth habit; a compact inflorescence; flowers double and with large spreading light pink petals.

* * * * *

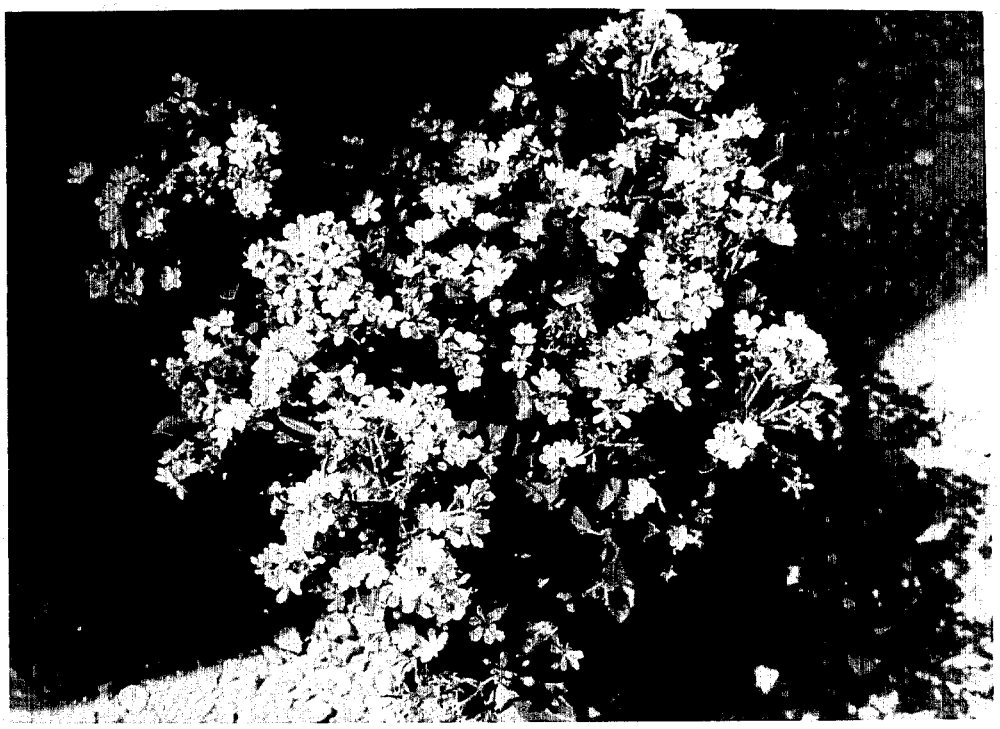
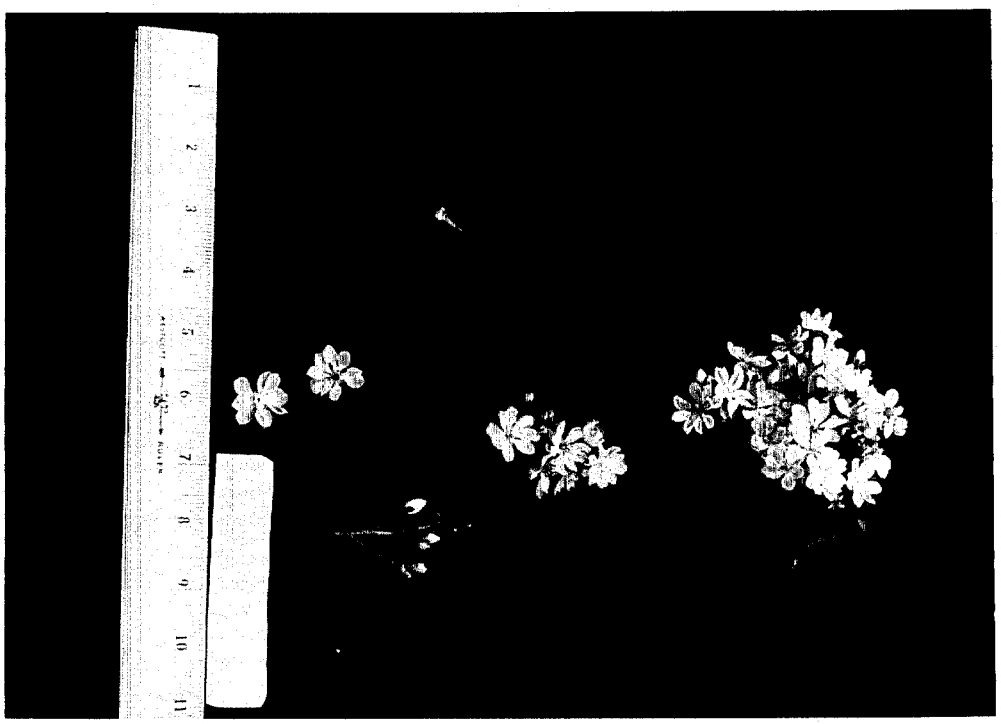

UNITED STATES PATENT AND TRADEMARK OFFICE

CERTIFICATE OF CORRECTION

PATENT NO. : Plant Pat. 05,212

DATED : March 27, 1984

INVENTOR(S) : William B. Usrey

It is certified that error appears in the above-identified patent and that said Letters Patent is hereby corrected as shown below: Title page:

In the Abstract line 6, "Enchantress" should read -- Moness --.

Column 1, lines 6 and 28, "Enchantress", each occurrence, should read -- Moness --.

Signed and Sealed this

Tenth Day of January, 1989

*Attest:*

DONALD J. QUIGG

*Attesting Officer*

*Commissioner of Patents and Trademarks*